US006911478B2

(12) United States Patent
Hrabie et al.

(10) Patent No.: US 6,911,478 B2
(45) Date of Patent: Jun. 28, 2005

(54) NITRIC OXIDE-RELEASING AMIDINE- AND ENAMINE-DERIVED DIAZENIUMDIOLATES, COMPOSITIONS AND USES THEREOF AND METHOD OF MAKING SAME

(75) Inventors: Joseph A. Hrabie, Fredrick, MD (US); Larry K. Keefer, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/808,272

(22) Filed: Mar. 23, 2004

(65) Prior Publication Data

US 2004/0180863 A1 Sep. 16, 2004

Related U.S. Application Data

(62) Division of application No. 10/349,228, filed on Jan. 22, 2003, now Pat. No. 6,750,254, which is a division of application No. 09/825,073, filed on Apr. 3, 2001, now Pat. No. 6,511,991, which is a division of application No. 09/446,653, filed as application No. PCT/US98/13723 on Jul. 1, 1998, now Pat. No. 6,232,336.
(60) Provisional application No. 60/051,690, filed on Jul. 3, 1997.

(51) Int. Cl.[7] .................... A61K 31/00; A61K 31/33; A61K 31/13
(52) U.S. Cl. .................... 514/631; 514/638; 514/773; 514/611; 514/934; 514/788.1; 514/183
(58) Field of Search ................ 514/631, 638, 514/773, 611, 934, 788.1, 183

(56) References Cited

U.S. PATENT DOCUMENTS

| | | | | |
|---|---|---|---|---|
| 4,954,526 | A | 9/1990 | Keefer | |
| 5,155,137 | A | 10/1992 | Keefer et al. | |
| 5,212,204 | A | 5/1993 | Keefer et al. | |
| 5,674,894 | A | 10/1997 | Currie et al. | 514/470 |
| 5,770,645 | A | 6/1998 | Stamler et al. | 524/416 |
| 6,232,336 | B1 | 5/2001 | Hrabie et al. | 514/402 |

FOREIGN PATENT DOCUMENTS

| | | |
|---|---|---|
| DD | 122080 | 9/1976 |
| WO | WO 93/13055 | 7/1993 |
| WO | WO 94/27957 | 12/1994 |
| WO | WO 95/05363 | 2/1995 |
| WO | 9505363 | * 2/1995 |
| WO | WO 96/36639 | 11/1996 |
| WO | WO 96/40665 | 12/1996 |

OTHER PUBLICATIONS

Bogdan C., PubMed Abstract 11577346, also cited as *Nat. Immunol.*, 2(10), 907–916 (2001).
Chabrier et al., PubMed Abstract 10442086, also cited as *Cell. Mol. Life Sci.*, 55(8–9), 1029–1035 (1999).
Derwent Abstract AN–85–047728, Derwent Publications Ltd., "New N, N'–dihydroxydiazenium Propanol Derivative for Prevention and Treatment of Apple Canker" (Jan. 14, 1985).
Feldman et al., *C&EN*, 26–38 (1993).
Freeman et al., "Alkaline Decomposition of Nitrosohydroxylamine Derivatives," *J. Org. Chem.*, 35(9), 3107–3110 (1970).
Le Corvoiser et al., PubMed Abstract 11324316, also cited as *J. Soc. Biol.*, 194(3–4), 143–149 (2000).
Nathan C., *FASEB*, 6, 3051–3063 (1993).
Oka et al., PubMed Abstract 12909236, also cited as *Int. J. Radiat. Oncol. Biol. Phys.*, 57(1), 217–221 (2003).
Turunen et al., PubMed Abstract 10817812, also cited as *Exp. Gerontol.*, 34(4), 567–574 (1999).
Volodarskii et al., "Preparation and Properties of N–nitroso–alpha–hydroxylamino Oximes," *Chemical Abstracts*, 85(21), abstract No. 15959w (1976).
Wang et al., PubMed Abstract 12856639, also cited as *Urol. Oncol.*, 21(2), 117–122 (2003).
Arnold et al., *Tetrahedron Letters*, 41, 8421–8424 (2000).
Boschi et al., *Bioorg. Med. Chem.*, 8, 1727–1732 (2000).
Cantuaria et al., *Cancer*, 88(2), (Abstract) 381–388 (2000).
Etchenique et al., *J. Am. Chem. Soc.*, 122, 3967–3968 (2000).
Hou et al., *Bioorg. Med. Chem. Lett.*, 9(15) (Abstract) 2255–2258 (1999).
Hrabie et al., *Bioconjugate Chem.*, 10, 838–842 (1999).
Severnia et al., *Biochem. and Mol. Bio. Int.*, 36(4), 913–925 (Jul. 1995).
Soulere et al., *Bioorg. Med. Chem. Lett.*, 10(12), 1347–1350 (2000).
Southan et al., *Nitric Oxide: Bio and Chem.*, 2(4), 270–286 (1998).
Tsumori et al., *Acta Biochem. Pol.*, 49(1), (Abstract) 139–144 (2002).

\* cited by examiner

*Primary Examiner*—Richard L. Raymond
*Assistant Examiner*—Sudhaker B. Patel
(74) *Attorney, Agent, or Firm*—Leydig, Voit & Mayer, Ltd.

(57) ABSTRACT

The present invention relates to nitric oxide-releasing amidine- and enamine-derived diazeniumdiolates, compositions comprising such compounds, methods of using such compounds and compositions, and to a method for the preparation of nitric oxide-releasing amidine- and enamine-derived diazeniumdiolates via the direct reaction of nitric oxide with amidines and enamines, and to a method of converting amines into such compounds.

29 Claims, No Drawings

NITRIC OXIDE-RELEASING AMIDINE- AND ENAMINE-DERIVED DIAZENIUMDIOLATES, COMPOSITIONS AND USES THEREOF AND METHOD OF MAKING SAME

CROSS REFERENCE TO RELATED APPLICATIONS

This application is a division of application Ser. No. 10/349,228, filed Jan. 22, 2003 now U.S. Pat. No. 6,750,254, which is a division of application Ser. No. 09/825,073, filed Apr. 3, 2001, now U.S. Pat. No. 6,511,911, which is a division of application Ser. No. 09/446,653, filed Nov. 30, 2000, now U.S. Pat. No. 6,232,336, which is the U.S. national stage of International Patent Application No. PCT/US98/13723, filed Jul. 1, 1998, which claims the benefit of Provisional Application No. 60/051,690, filed Jul. 3, 1997, all of which are incorporated herein by reference.

FIELD OF THE INVENTION

The present invention relates to nitric oxide-releasing amidine- and enamine-derived diazeniumidiolates, to compositions comprising such compounds, to methods of using such compounds and compositions, to a method for the preparation of nitric oxide-releasing amidine- and enamine-derived diazeniumdiolates via the direct reaction of nitric oxide with amidines and enamines, and to a method of converting amines into such compounds.

BACKGROUND OF THE INVENTION

Nitric oxide (NO) has been implicated as part of a cascade of interacting agents involved in a wide variety of bioregulatory processes, including the physiological control of blood pressure, macrophage-induced cytostasis and cytotoxicity, and neurotransmission (Moncada et al., "Nitric oxide from L-Arginine: A Bioregulatory System," *Excerpta Medica,* International Congress Series 897, Elsevier Science Publishers B. V.: Amsterdam (1990); Marletta et al., *Biofactors* 2: 219–225 (1990); Ignarro, *Hypertension (Dallas)* 16: 477–483 (1990); Kerwin et al., *J. Med. Chem.* 38: 4343–4362 (1995); and Anggard, *Lancet* 343: 1199–1206 (1994)). Given that NO play a role in such a wide variety of bioregulatory processes, great effort has been expended to develop compounds capable of releasing NO. Some of these compounds are capable of releasing NO spontaneously, e.g., by hydrolysis in aqueous media, whereas others are capable of releasing NO upon being metabolized (Lefer et al., *Drug Future* 19: 665–672 (1994)).

Keefer et al. (U.S. Pat. Nos. 4,954,526; 5,039,705; 5,155,137; 5,208,233 and 5,405,919 and related patents and patent applications, all of which are incorporated herein by reference) disclose, among others, the use of certain nucleophile/nitric oxide adducts as NO-releasing agents, i.e.,

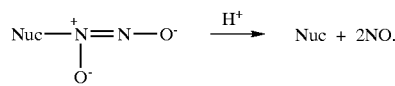

in which the nucleophilic residue (Nuc) is a primary amine, a secondary amine or a polyamine. Although such adducts offer many advantages over other currently available nitric oxide-releasing compounds, one disadvantage presented by the use of such adducts as pharmaceutical agents is the potential risk of release of nitrosamines, which are carcinogenic, upon decomposition and release of NO. Another disadvantage of the adducts of primary amines is that they can be unstable even as solids due to a tendency to form traces of potentially explosive diazotates.

Several types of compounds of the general structure

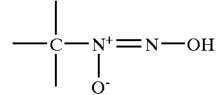

have been known for many years. Traube (*Liebigs Ann. Chem:* 300: 81–123 (1898)) reported the preparation of a number of such compounds and noted that treatment of the compounds with acid produced a "brown gas." Although brown gas suggests the release of NO, given that a brown gas also may be produced in the disproportionation of nitrite, the release of brown gas by the compounds prepared by Traube is not, in and of itself, evidence of NO release. Compounds of the structural type reported by Traube are known to require harsh treatment with mineral acids to release any gas which is, of course, incompatible with a biological utility.

Another compound, which has the structure

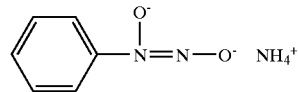

and which has been named cupferron, has been shown by Kubrina et al., *Izvestia Akademii Nauk SSSR Seriia Biologicheskaia* 6: 844–850 (1988)) to generate NO in vivo. In addition, the antibiotics alanosine (C(O)(OH)CH(NH$_2$)CH$_2$N(O)=NOH) and dopastin (CH$_3$CH=CHC(O)NHCH$_2$CH(i-propyl)—N(O)=NOH), as well as cupferron, have been shown to release NO in vivo by enzymatic oxidation (Alston et al., *J. Biol. Chem.* 260: 4069–4074 (1985)).

More recently, Keefer et al., in U.S. Pat. No. 5,212,204, have broadly described that an organic moiety may be linked via carbon to the N$_2$O$_2^-$ group. This patent does not disclose an amidine or enamine structure as the nucleophile, nor does it teach the nature of the structural characteristics that an organic moiety must possess to cause the resulting N$_2$O$_2^-$ group to be a nitric oxide donor.

Some N$_2$O$_2^-$-containing compounds have been disclosed to be useful as curing agents in rubber manufacture, anti-knock additives for gasoline, indicator dyes, explosives, corrosion inhibitors and fungicides (Danzig et al., U.S. Pat. No. 3,309,373; Wiersdorff et al., *Chem Abstracts* 77: 48034f (1972); Massengale, U.S. Pat. No. 2,635,978; and Metzger et al., U.S. Pat. No. 2,954,314). However, the mechanism of the reported action of these compounds was not described.

In this regard, a recent study of the N$_2$O$_2^-$ group (Taylor et al., *J. Org. Chem.* 60: 435–444 (1995)) proposed a mechanism for the observed NO release. The proposed mechanism was based on quantum mechanical calculations which showed protonation at the terminal oxygen to be most favored thermodynamically in the case of N bound N$_2$O$_2^-$.

None of the above disclosures, however, mention anything about the release of nitroxyl (HNO, which, at the physiological pH of 7.4, exists as NO$^-$) by this functional group. Recent results suggest that, under certain conditions, many classes of "NO donors" may release some NO$^-$ (see the discussions for nitrosothiols and diazeniumdiolates as well as the table of NO donors in Feelisch et al., Donors of Nitrogen Oxides, *In Methods in Nitric Oxide Research*, M. Feelisch and J. S. Stamler, Eds., Ch. 7, pp. 71–115, John Wiley and Sons, New York (1996)).

To date, there are three compounds used to generate HNO in solution. One compound, Angeli's salt, which is the standard HNO source (Fukuto et al., *J. Pharm. Exp. Ther.* 263: 546–551 (1992)), is, of course, an inorganic salt. The other two compounds, acetylated Piloty's acid (Smith et al., *J. Amer. Chem. Soc.* 82: 5731–5740 (1960)) and benzoylated hydroxycyanamide (Lee et al., *J. Med. Chem.* 35 3648–3652 (1992)) are promising inhibitors of aldehyde dehydrogenase. However, even in these compounds, there is debate as to whether the observed physiological effects are attributed to NO, or to $NO^-$. For example, Piloty's acid has been shown to release NO oxidatively under physiological conditions (Zamora et al., *Biochem. J.* 312: 333–339 (1995)).

Reports that superoxide dismutase can prolong the effects of NO via its reversible reduction to $NO^-$ (Murphy et al., *PNAS USA* 88: 10860–10864 (1991)) and that $NO^-$, itself, exhibits potent activity as a vasodilator (Fukuto et al., *J. Pharm. Exp. Ther.* 263: 546–551 (1992)) and as an inhibitor of aldehyde dehydrogenase (Lee et al., *J. Med. Chem.* 35: 3648–3652 (1992)) suggest that compounds, which release either NO or $NO^-$ or mixtures of the two, are potentially useful pharmaceutical agents and may even offer advantages over compounds that just release NO.

Despite the extensive literature available on NO and nitric oxide-releasing compounds, there remains a need for stable nitric oxide-releasing compounds in which the nitric oxide-releasing group $N_2O_2^-$ is bonded directly to a carbon atom and which can be prepared from compounds that do not include a nitrogen atom suitable for conversion to a diazeniumdiolate.

Accordingly, it is an object of the present invention to provide a chemical structural framework having an atomic and electronic arrangement such that an $N_2O_2^-$ functional group attached thereto will serve as a spontaneous NO and/or $NO^-$ donor. It is a further object of the present invention to provide a method for producing novel NO and/or $NO^-$-releasing diazeniumdiolates in which the $N_2O_2$—group is bound to a carbon atom. Another object of the present invention is to provide NO- and/or $NO^-$-releasing derivatives of amidines and enamines. A related object of the present invention is to provide NO— and/or $NO^-$-releasing derivatives of known pharmaceutical agents. A more specific object is to provide NO- and/or $NO^-$-releasing derivatives of known pharmaceutical agents whose nitrogen atoms do not provide suitable N-diazeniumdiolates as nitric oxide donors. Yet another object of the present invention is to provide compositions comprising NO- and/or $NO^-$-releasing derivatives of amidines and enamines. A further object of the present invention is to provide methods of using NO- and/or $NO^-$-releasing derivatives of amidine and enamine compounds, and compositions thereof. These and other objects of the present invention, as well as additional inventive features, will be apparent from the description of the invention provided herein.

BRIEF SUMMERY OF THE INVENTION

The present invention provides NO- or $NO^-$-releasing diazeniumdiolates which are derived from an enamine or an amidine and in which the $N_2O_2^-$ functional group is bonded to a carbon atom. The present invention also provides compositions comprising such diazeniumdiolate compounds, and methods of using such compounds and compositions. The present invention further provides a method of producing an NO- or $NO^-$-releasing enamine- or amidine-derived diazeniumdiolate. Additionally, the present invention provides a method for the preparation of an NO- and/or $NO^-$-releasing amidine derivative from an existing amino compound. The method comprises reaction of the amino compound with an acetamidating reagent followed by reaction with nitric oxide gas.

DETAILED DESCRIPTION OF THE INVENTION

In accordance with one aspect of the invention, there is provided a novel class of nitric oxide-nucleophile adducts or diazeniumdiolates having an amidine- or enamine-derived chemical linkage in which the $N_2O_2^-$ functionality is bound directly to a carbon atom of the linkage. The amidine- or enamine-derived chemical linkage which includes the $N_2O_2^-$ functional group is represented by the schematic formula depicting the characteristic connectivity:

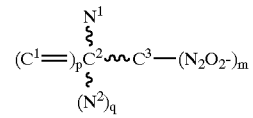

wherein
$C^2 \sim C^3$ means either $C^2$—$C^3$ or $C$=$C^3$
m is 1 or 2
q is 0 or 1
p is 0 or 1
provided that
(1) $C^2$ is tetravalent, and bound to two or more of $C^2$, $C^3$, $N^1$ and $N^2$;
(2) when p=1, then q=0 and $C^2 \sim C^3$ means $C^2$—$C^3$; or
(3) when p=0, and q=1, then $C^2 \sim C^3$ means either (i) $C^2$p=$C^3$ or (ii) $C^2$—$C^3$ where $C^2$—$N^1$ means $C^2$=$N^1$;
(4) when $C^2 \sim C^3$ means $C^2$—$C^3$ and q=1 and p=0 $C^2 \sim N^1$ and $C^2 \sim N^2$ means

It will be appreciated by those skilled in the art that due to the nature of the synthesis reaction employed as disclosed herein, the double bond in all cases would originally form as a C=N and then tautomerize if that is possible due to the presence of a C—H β to $N^1$. The double bond typically tautomerizes to the more thermodynamically favored structure. However, less thermodynamically favored tautomers may occur and have been observed depending on conditions such as solvent or the like. In compounds where there is no H in the β position to $N^1$ no tautomerization occurs. Thus, the present invention contemplates all NO-releasing diazeniumdiolates which include an amidine- or an enamine-derived chemical linkage in which the $N_2O_2^-$ functional group is bound to a carbon atom irrespective of the tautomer that is thermodynamically favored. The electron movement or tautomerization for the enamines and for the amidines is the same conceptually, but in the case of the enamines it is the lone pair of electrons associated with the nitrogen atom which must be used in the reaction since there is no H on the enamine nitrogen.

The amidine- and enamine-based diazeniumdiolates of the present invention are advantageous in several respects.

These compounds are not expected to decompose to carcinogenic nitrosamines. The diazeniumdiolates of the present invention exhibit the full range of water solubility. Some of the diazeniumdiolates of the present invention are thus particularly useful where water insolubility is desirable, such as in stents, implants, prostheses and the like. Many diazeniumdiolates of the present invention are characterized by long-term slow release of NO and can be used in coatings or the like. Further, these compounds do not bleed out of the coating, even after the NO has been released. The diazeniumdiolates of the present invention are very stable solids and in solution are more heat stable than the previously described nitrogen analogs. Some can be recrystallized from boiling solvents without decomposition.

In keeping with the invention, the amidine-derived diazeniumdiolates may be further described in accordance with the following formulas:

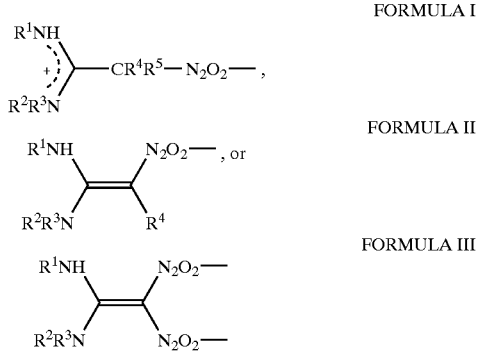

wherein $R^1$—$R^5$ can be a wide variety of substituents without departing from the scope of the present invention owing to the fact that any compound which includes the characteristics of the chemical linkage identified above is contemplated herein.

Thus, in the compounds of Formula I, II or III, $R^1$—$R^3$ are independently chosen from hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted $C_{3-8}$ cycloalkyl, a $C_{3-8}$ heterocyclic ring bound through a carbon atom and in which the heteroatom is oxygen or nitrogen, a substituted or unsubstituted naphthyl, a substituted or unsubstituted tetrahydronaphthyl, a substituted or unsubstituted octrahydronaphthyl, benzyl or substituted benzyl, substituted with up to three substituents, or a substituted or unsubstituted phenyl, substituted with up to three substituents.

In the compounds of Formula I, II or III, $R^4$ and $R^5$ are independently hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted benzyl, a substituted or unsubstituted phenyl, a substituted or unsubstituted piperazino, or a substituted or unsubstituted morpholino. $R^4$ and $R^5$ also can be amino, an unsubstituted or substituted alkylamino, carboxyalkylamino, carboxydialkylamino, an unsubstituted or substituted tolyl, xylyl, anisyl, mesityl, nitro, an unsubstituted or substituted arylamino, an unsubstituted or substituted dialkylamino, an unsubstituted or substituted diarylamino, an unsubstituted or substituted acetyl, an unsubstituted or substituted acetoxy, carboxy, an unsubstituted or substituted carboxyalkyl, such as an unsubstituted or substituted carboxymethyl or an unsubstituted or substituted carboxyethyl, an unsubstituted or substituted alkylcarbonyl, thiol, an unsubstituted or substituted alkylthio, an unsubstituted or substituted alkoxy, carboxamido, an unsubstituted or substituted alkylcarboxamido, an unsubstituted or substituted dialkylcarboxamido, an unsubstituted or substituted phenoxy, an unsubstituted or substituted benzyloxy, an unsubstituted or substituted nitrophenyl, phenylcarbonyl, benzylcarbonyl, trialkylsilyl.

When any of the groups indicated above for $R^1$—$R^5$ are identified as being substituted, such as when the $C_{1-12}$ straight chain alkyl, the $C_{3-12}$ branched chain alkyl, the $C_{3-12}$ straight chain olefinic, the $C_{3-12}$ branched chain olefinic, the $C_{3-8}$ cycloalkyl, the benzyl, piperazino, morpholino, alkylamino, arylamino, acetyl, acetoxy, carboxy, carboxymethyl, alkoxy or the like are substituted, they can be substituted with any moiety that does not destroy the NO-releasing character of the compounds and which, preferably, is biologically compatible. Accordingly, substituents to the substituted $R^1$—$R^5$ groups can include hydroxy, alkoxy, acyloxy, halo or benzyl, acetyl, carboxyl, carboxyalkyl, such as carboxymethyl, carboxyethyl, carboxyalkylamido, carboxydialkylamido, carboxamido, amino, alkylamino, dialkylamino, alkylcarbonyl, arylamino, diarylamino, cyano, tolyl, xylyl, mesityl, anisyl, pyrrolidinyl, formyl, dioxane, thiol, alkylthiol, aryl, heteroaryl, such as pyran, pyrrole, furan, thiophene, thiazole, pyrazole, pyridine, or pyrimidine, phenoxy, benzyloxy, phenylcarbonyl, benzylcarbonyl, nitrophenyl trialkylsilyl, nitro, sulfonyl, nitrobenzyl, trialkylammonium, alkyl, cycloalkyl, tetrahydrofuranyl, tetrahydropyranyl, piperidinyl or morpholinyl.

The substituents $R^1$, $R^2$, $R^3$, $R^4$ and $R^5$, in various combinations, and together with the nitrogen atom or carbon atom to which they are bonded, can form unsubstituted or substituted cyclic or unsubstituted or substituted heterocyclic rings. The rings that are formed are four member rings or layers. For example, $R^1$ and $R^2$ together with the nitrogen atoms to which they are bonded can form a $C_{2-8}$ heterocyclic ring. $R^1$ and $R^4$ together with the nitrogen atom to which $R^1$ is bonded and with the carbon atom to which $R^4$ is bonded can form a $C_3$–$C_8$ heterocyclic ring. Similarly, $R^2$ and $R^3$ can form a $C_{3-8}$ heterocyclic ring with the nitrogen atom to which they are bonded. The heterocyclic ring can also include up to one additional heteroatom, such as oxygen, nitrogen or sulfur.

The heterocyclic rings formed by the different combinations of $R^1$, $R^2$, $R^3$, $R^4$ and $R^5$ can be, for example, a piperazino, a morpholino, a hexamethyleneimino, an imidazolyl, a pyrrolidino, a piperidino or the like. Likewise, $R^4$ and $R^5$ together with the carbon atom to which they are bonded can form a $C_{3-8}$ cycloalkyl, or a heterocyclic such as tetrahydrofuranyl, dioxanyl or the like. Further, $R^4$ and $R^5$ together with the carbon atom to which they are bonded can form a 1,4-benzodioxane, 1,3-benzodioxole, tetrahydronaphthlene, octahydronaphthalene, piperazine, morpholine, tetrahydroquinoline, tetrahydroquinoxaline, or tetrahydroisoquinoline.

Each of the cyclic or heterocyclic rings formed with $R^1$ and $R^2$, or $R^2$ and $R^3$, or $R^1$ and $R^4$, or $R^4$ and $R^5$ can be substituted with one or more substituents, including, by way of example, $C_{3-8}$ cycloalkyl, alkoxy, benzyl, fused benzene, phenyl, an alkoxy, acetyl, carboxyl, carboxymethyl, carboxyethyl, carboxamido, amino, alkyl amino, dialkylamino, pyrrolidine, dioxane, thiol or alkylthiol, or a heteroaryl such as pyran, pyrrole, furan, thiophene, thiazole, pyrazole, pyridine, or pyrimidine.

The compounds of the present invention can be derived from existing pharmaceutical agents that contain the amidine group. For example, a compound of Formula III preferably is one in which $R^1$ and $R^2$ are hydrogen and $R^3$ is the entire substituent attached to an amine of a pharmaceutical agent such as, for example, tryptamine, serotonin, histamine, valcyclovir, adenosine, thyroxine, guanine, guanosine, ubenimex, glucosamine, mannosamine, mycosamine, sphingosine, thienamycin, penicillamine and rimantadine. Similarly, for example, the present invention provides a compound of Formula III, in which $R^1$ and $R^2$ are hydrogen and $R^3$ is the entire substituent attached to an amine of an amino acid. The amino acid is preferably lysine, tryptophan or hydroxy-tryptophan.

The present invention also provides compounds of

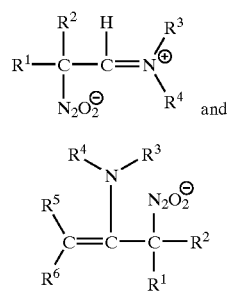

FORMULA IV and

FORMULA V wherein $R^1$—$R^6$ can be a wide variety of substituents without departing from the scope of the present invention owing to the fact that any compound which includes the characteristics of the chemical linkage identified above is contemplated herein.

Thus, in the compounds of Formula IV and Formula V, $R^1$, $R^2$, $R^5$ and $R^6$ are independently hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted benzyl, a substituted or unsubstituted piperazino, a substituted or unsubstituted morpholino, amino, an unsubstituted or substituted alkylamino, an unsubstituted or substituted arylamino, an unsubstituted or substituted dialkylamino, an unsubstituted or substituted diarylamino, carboxyalkylamino, carboxydialkylamino, cyano, tolyl, xylyl, anisyl, mesityl, nitro, an unsubstituted or substituted acetyl, an unsubstituted or substituted acetoxy, carboxy, an unsubstituted carboxyalkyl, such as an unsubstituted or substituted carboxymethyl, or an unsubstituted or substituted carboxyethyl, an unsubstituted or substituted alkylcarbonyl, thiol, an unsubstituted or substituted alkylthio, an unsubstituted or substituted alkoxy, carboxamido, an unsubstituted or substituted alkylcarboxamido, or an unsubstituted or substituted dialkylcarboxamido.

In the compounds of Formula IV and V, $R^3$ and $R^4$ are independently chosen from hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted $C_{3-8}$ cycloalkyl, a $C_{3-8}$ heterocyclic ring bound through a carbon atom and in which the heteroatom is oxygen or nitrogen, a substituted or unsubstituted naphthyl, a substituted or unsubstituted tetrahydronaphthyl, a substituted or unsubstituted octahydronaphthyl, benzyl or substituted benzyl, substituted with up to three substituents, or a substituted or unsubstituted phenyl, substituted with up to three substituents. Such compounds are advantageous because they are more "organic" than polyamines, such that simple aromatic enamines can be made to be water-insoluble, yet release NO, and to be heat-stable.

When any of the groups indicated above for $R^1$—$R^5$ are identified as being substituted, such as the $C_{1-12}$ straight chain alkyl, the $C_{3-12}$ branched chain alkyl, the $C_{3-12}$ straight chain olefinic, the $C_{3-12}$ branched chain olefinic, the $C_{3-8}$ cycloalkyl, the benzyl, piperazino, morpholino, alkylamino, arylamino acetyl, acetoxy carboxy, carboxymethyl alkoxy or the like, they can be substituted with any moiety that does not destroy the NO-releasing character of the compounds and which, preferably, is biologically compatible. Accordingly, substituents to the substituted $R^1$—$R^5$ groups can include hydroxy, alkoxy, acyloxy, halo or benzyl, acetyl, carboxyl, carboxyalkyl, such as carboxymethyl, carboxyethyl, carboxyalkylamido, carboxydialkylamido, carboxamido, amino, alkyl amino, dialkylamino, alkylcarbonyl, arylamino, diarylamino, tolyl, xylyl, mesityl, anisyl, pyrrolidine, formyl, dioxane, thiol, alkylthiol, aryl, heteroaryl, such as pyran, pyrrole, furan, thiophene, thiazole, pyrazole, pyridine, or pyrimidine, phenoxy, benzyloxy, phenylcarbonyl, benzylcarbonyl, nitrophenyl trialkylsilyl, nitro.

The groups $R^1$—$R^6$ of the compounds of Formula IV and Formula V in various combinations, and together with the nitrogen atom or carbon atom to which they are bonded and intervening atoms, can form heterocyclic rings. For example, and not in limitation, a compound of Formula V in which $R^3$ and $R^4$, together with the nitrogen atom to which they are bonded, can form a $C_{3-8}$ heterocycle. The heterocycle can be further substituted with a heteroatom. As another example, in the Formula V compound, $R^1$ and $R^6$, together with the C=C—C through which they are bonded, can form a substituted or unsubstituted $C_{3-12}$ cycloalkyl. Similarly, for a compound of Formula IV, $R^2$ and $R^3$, together with the nitrogen to which $R^3$ is bonded, can form a $C_{3-8}$ heterocycle. The heterocycle can be further substituted with a heteroatom, or an aromatic ring, which can be substituted with a $C_{1-6}$ alkyl or a $C_{1-6}$ alkoxy. Also, $R^5$ and $R^4$ can form a $C_{3-8}$ heterocycle, which can also be substituted.

In Formulas IV and V, $R^3$ and $R^4$ together with the nitrogen atom to which they are bonded can form a $C_{3-8}$ heterocyclic ring or a $C_{3-8}$ substituted heterocyclic ring or a $C_{3-8}$ unsubstituted or substituted heterocyclic ring containing up to two additional heteroatoms selected from the group O, S, N.

Also, $R^5$ and $R^6$ together with the carbon to which they are bonded can form a substituted or unsubstituted $C_{4-8}$ cycloalkyl.

With respect to the compounds of Formulas I, II and III, $R^1$—$R^5$ can be selected such that they represent the substituents attached to the amidine of nasal decongestants and α-adrenergic antagonists such as tetrahydrozoline, idazoxan, phentolamine, xylometazoline and the like.

In accordance with another aspect of the invention, there is provided a method for the preparation of the amidine- and enamine-derived NO-releasing compounds described herein. In one embodiment, the method comprises reacting an amidine, preferably an amidine of Formula Ia, IIa or IIIa, with gaseous NO in acetonitrile or a similar solvent to produce an $N_2O_2^-$-containing compound. $R^1$ and $R^4$ together with the nitrogen atom to which $R^1$ is bonded and with the carbon atom to which $R^4$ is bonded can form a $C_3$–$C_8$ heterocyclic ring.

The solvent is preferably chosen so that the starting amidine or enamine is soluble whereas the resulting $N_2O_2^-$-containing product is insoluble and so precipitates as it forms in order to drive the reaction to completion. Anhydrous and neutral solvents such as acetonitrile, tetrahydrofuran, dioxane and ether are preferred because they do not cause hydrolysis of the water-sensitive amidines and enamines. However, it is anticipated that low yields of the desired products can also form in partly aqueous and/or basic solvents such as NaOMe in methanol or wet tetrahydrofuran among others, and such solvents may also be used.

The resulting compound in accordance with the method of the invention contains either one or two $N_2O_2^-$ functional groups depending upon the structure of the amidine reactant, as, for example, shown below.

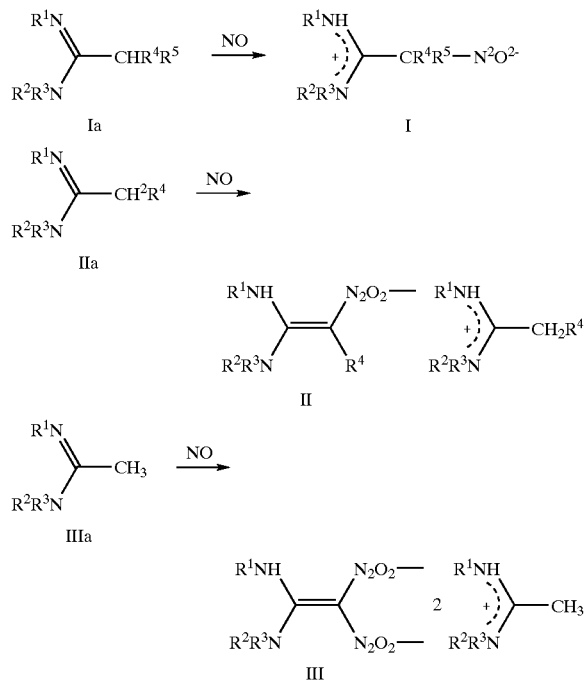

Methods for the preparation of the amidines, such as those of Formulas Ia, IIa and IIIa, are well known and have been reviewed in two reference books, Gautier et al., "preparation and Synthetic Uses of Amidines," Chapter 7 in *The Chemistry of Amidines and Imidates*, Editor: Patai, pp. 283–348, Wiley, 1975, and Boyd, "Recent Advances in the Synthesis of Amidines," Chapter 7 in *The Chemistry of Amidines and Imidates,* Volume 2, Editors: Patai and Rappoport, pp. 339–367, Wiley, 1991. These methods can be used by those skilled in the art to prepare a wide variety of amidines which can then be made into NO-releasing diazeniumdiolates in accordance with the invention.

By way of example and not in limitation, the preparation of an NO-releasing amidine-derived diazeniumdiolate can be illustrated by the reaction of 2-methyl-2-imidazoline with NO as follows:

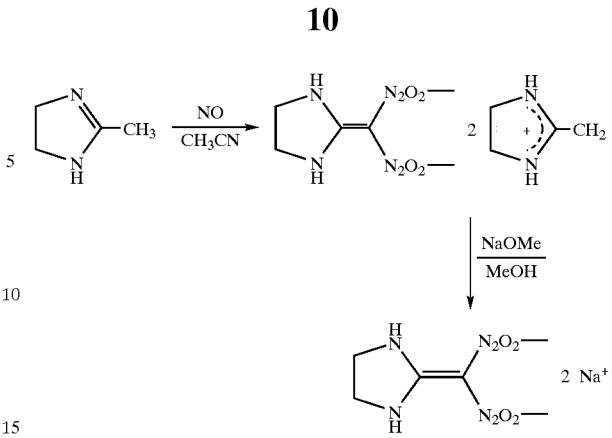

Although the initial reaction products are the amidinium salts (either intramolecular or intermolecular), standard metathesis reactions can be employed to change the cation to any pharmaceutically acceptable ion. This is illustrated above by the reaction involving sodium methoxide in methanol, which produces the disodium salt. Also, by varying the synthesis procedures, the intramolecular or intermolecular salt or a mixture thereof can be obtained; the reaction of 2-methyl-2-imidazoline with NO in NaOMe/MeOH to directly form the sodium salt is an example of such a reaction.

While applicants do not wish to be bound to any particular theory, the above reactions are believed to be explained by the reaction of NO with the little exploited enediamine tautomers of the amidines. The enediamine tautomers are known to exist in solution and were first proposed to explain deuterium exchange in NMR solutions as follows (Isagulyants et al., *Zh. Prikl. Khim.* 41: 1585–1590 (1968); also, in *Chem. Abstracts* 70: 11629h (1969)):

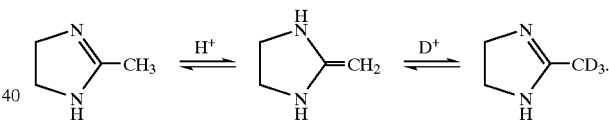

Accordingly, while not being bound to any particular theory, it is believed that the reaction of the above undeuterated compound with an NO dimer is as follows:

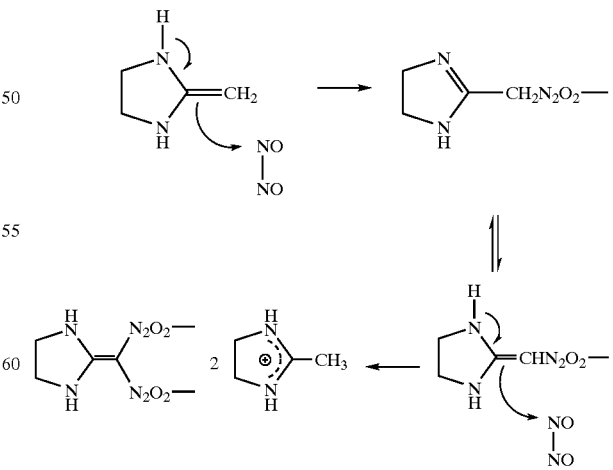

The reaction is believed to stop at this stage due to steric hindrance and/or precipitation of the product from solution.

When either the amidinium or sodium salt of the NO-releasing diazeniumdiolate derived from 2-methyl-2-imidazoline was dissolved in water and acidified, a voluminous gas evolution resulted and the solution turned blue in color and remained so for many hours after gas evolution had ceased. When the experiment was repeated at pH 7.4, the evolving gas was identified as a mixture of 2 parts NO (determined by chemiluminescence) and 1 part $N_2O$ (determined by gas chromatography). Nitrous oxide ($N_2O$), being the end product of HNO dimerization and dehydration, provided a measure of HNO production via the equation (Nagasawa et al., *J. Med. Chem.* 33: 3122–3124 (1990)):

Again, while not wishing to be bound to any particular theory, it is believed that the partial mechanistic explanation for these observations is as follows:

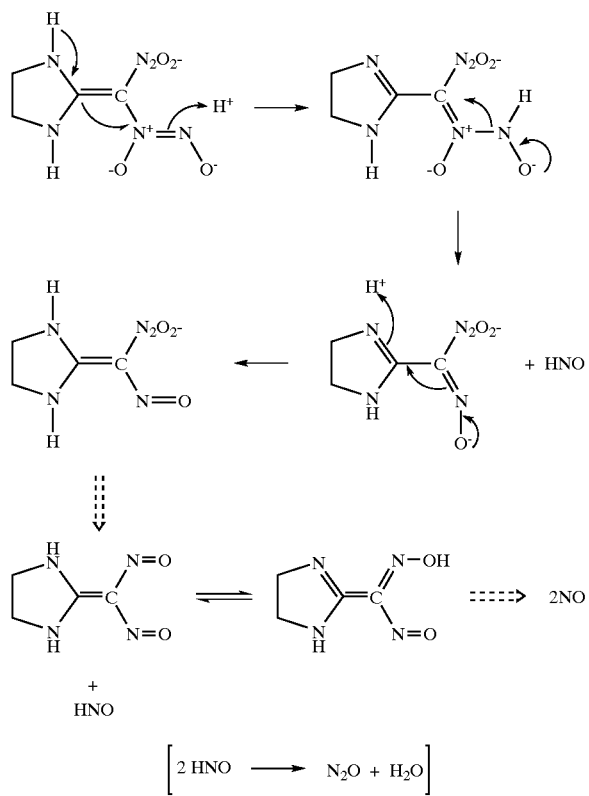

The last step in this mechanism is not well understood but has precedent in the known release of NO by FK409 and closely related compounds which are used as standard sources of NO (Kita et al., *Eur. J. Pharmacol.* 257: 123–130 (1994)). Although this mechanism is one explanation for the observed NO and $N_2O$ release, it is a very incomplete representation of what actually happens to any given compound in aqueous solution. Specifically, amidines are known to be subject to hydrolysis at rates that range from very slow, such as for 2-methyl-2-imidazoline (Haake et al., *J. Org. Chem.* 35: 4063–4067 (1970))

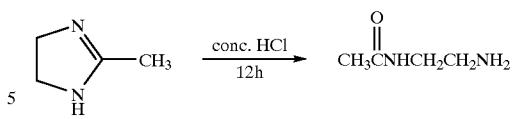

to very fast for acetamidine (Davies et al, *Chem. Ind.* (*London*): 628 (1958)).

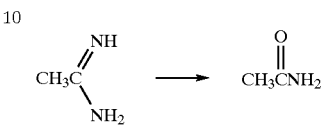

Thus, at any intermediate stage of HNO or NO release, the amidino group could hydrolyze and no further gas would be generated. A compound in which the amidine hydrolyzes rapidly would release much HNO but very little NO, whereas a compound in which the amidine hydrolyzes slowly would have time for NO release, which is the last step, and would thus release a larger mount of NO. In this regard, compounds of Formula I (as set forth above) cannot be hydrolyzed by the above mechanism. It is believed that these mono-$N_2O_2^-$ derivatives break down via two competing pathways, one of which appears to be simple reversal of the synthesis step to release NO, while the other may be a single scission to yield one molecule of HNO and a mono-C-nitroso compound. Since the amidino tautomers cannot come into conjugation with this nitroso group, it does not serve as a source of NO, and since hydrolysis of the amidine competes with the first pathway, compounds derived from amidines of formula I release only small amounts of NO, but over a long period of time. In such cases, the reaction of an amidine with NO results in a sterically hindered compound of formula I, which is apparently inclined to break apart differently than previously reported, less hindered $N_2O_2^-$ compounds.

In another embodiment of the present inventive method, an enamine, preferably an enamine of Formula IV or V, is reacted with NO to produce an $N_2O_2^-$ containing compound. Enamines are prepared from an equimolar mixture of an aldehyde or ketone and a secondary amine via dehydration as follows.

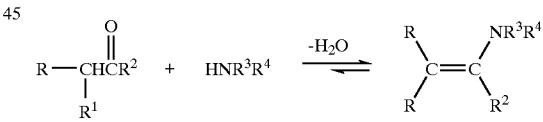

Methods for preparing enamines and lengthy discussions of their properties are readily available to synthetic chemists (see, e.g., Hickmott, *Tetrahedron* 38: 1975–2050 (1982); Hickmott, *Tetrahedron* 38: 3363–3446 (1982); Cook, *Enamines: Synthesis, Structure and Reactions,* Marcel Dekker, New York (1988); and Szmuszkovicz, *Enamines,* Vol. 4 of *Adv. in Org. Chem. Methods and Results,* Wiley Interscience, New York (1963)). Although literally thousands of carbonyl compounds are used in this reaction, the amines are usually limited to a select few, such as dimethylamine, diethylamine, piperidine, pyrrolidine, morpholine, and N-methylaniline.

Unlike the amidine-derived compounds, the enamine-derived diazeniumdiolates do not appear to release any $NO^-$ or $N_2O$. Rather, they release small amounts of NO over prolonged periods of time (e.g., 1 week in phosphate-buffered saline). As with amidine-derived compounds, the mechanism of NO release is complicated by a competing hydrolysis mechanism as set forth below.

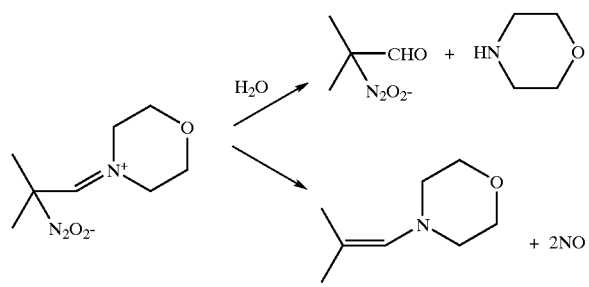

It will be appreciated by those of ordinary skill in the art that either the amidine-derived or enamine-derived diazeniumdiolates in accordance with the present invention can be formed as a salt, and preferably, a biologically acceptable salt. Accordingly, the counterion is preferably any biologically acceptable acceptable counterion. Such counterions can include, but are not limited to, sodium ion, potassium ion, quaternary ammonium ions, and the like.

Also provided by the present invention is a method of producing a nitric oxide-releasing compound from a compound containing a primary amine and/or a secondary amine. The method comprises (a) treating the compound containing a primary amine and/or a secondary amine with an acetamidating agent, by which is meant an organic chemical reagent capable of transferring the $CH_3C(=NH)^-$ group from itself to another molecule. Such reagents are generally acetimidates, for example, ethyl acetimidate, or thioimidates, for example, benzyl thioacetimidate. The preferred reagent for use in the context of this method is that described in Shearer et al., *Tetrahedron Letters* 38(2): 179–182 (1997), so as to form an acetamidine derivative of the compound containing the primary amine and/or secondary amine, and (b) treating the acetamidine derivative with nitric oxide gas to form an amidine-derived diazeniumdiolate. This method in accordance with the invention provides a method for preparing an amidine-based diazeniumdiolate in which the NO-releasing $N_2O_2^{31}$ functional group is bound to a carbon atom rather than to the original primary or secondary amine. In this way, many primary and secondary amine-containing drugs can be subjected to the acetamidating reagent to produce the amidine which can then be converted to the diazeniumdiolate. This is advantageous particularly in the case of primary amines where the $N-N_2O_2^-$ functionality is not very stable.

As is well known in the art, nitric oxide and compounds comprising $N_2O_2^-$ functional groups can have a wide range of utilities, in part because of the multifaceted role of nitric oxide in bioregulatory processes. Accordingly, the present invention also provides a composition, including a pharmaceutical composition, comprising a present inventive diazeniumdiolate. Preferably, the pharmaceutical composition additionally comprises a pharmaceutically acceptable carrier.

One skilled in the art will appreciate that suitable methods of administering a diazeniumdiolate composition of the present invention to an animal, such as a mammal, are available, and, although more than one route can be used to administer a particular composition, a particular route can provide a more immediate and more effective reaction than another route. Pharmaceutically acceptable carriers are also well-known to those who are skilled in the art. The choice of carrier will be determined, in part, both by the particular composition and by the particular method used to administer the composition. Accordingly, there is a wide variety of suitable formulations of the pharmaceutical compositions of the present invention.

Formulations suitable for oral administration can consist of (a) liquid solutions, such as an effective amount of the diazeniumdiolate dissolved in diluents, such as water or saline, (b) capsules, sachets or tablets, each containing a predetermined amount of the active ingredient, as solids or granules, (c) suspensions in an appropriate liquid, and (d) suitable emulsions. Solutions may also be formulated using known preservatives for amidine-based nasal decongestants.

Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The diazeniumdiolates of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compositions employed (taking into consideration, at least, the rate of NO evolution, the extent of NO evolution, and the bioactivity of any decomposition products derived from the diazeniumdiolates) and the condition of the animal, as well as the body weight of the animal to be treated. The size of the dose also will be determined by the existence, nature, and extent of any adverse side-effects that might accompany the administration of a particular composition. A suitable dosage for internal administration is 0.01 to 100 mg/kg per day. A preferred dosage is 0.01 to 35 mg/kg per day. A more preferred dosage is 0.05 to 5 mg/kg per day. A suitable concentration of a enamine- or amidine-derived diazeniumdiolate in pharmaceutical compositions for topical administration is 0.05 to 15% (by weight). A preferred concentration is from 0.02 to 5%. A more preferred concentration is from 0.1 to 3%.

In view of the above, the present invention provides methods of using a nitric oxide-releasing amidine- or enamine-derived diazeniumdiolate. In one embodiment, a method of treating an animal, such as a mammal, with a biological disorder treatable with nitric oxide, is provided. The method comprises administering to the animal, e.g., the mammal, in need thereof an amount of an enamine- or amidine-derived diazeniumdiolate sufficient to treat the biological disorder in the animal. In this embodiment, "biological disorder" can be any biological disorder, including hypertension, restenosis, impotency, and a biological disorder due to a genetic defect or infection with an infectious agent, such as a virus, bacterium or parasite, as long as the disorder is treatable with nitric oxide.

With regard to the above, NO- and/or $NO^-$-releasing compounds derived from amidines are advantageous inasmuch as amidines are present in many already approved medicinal agents, e.g., tranquilizers, α-adrenergic antagonists, like phentolamine, and nasal decongestants. Specific examples include tolazoline and diazoxide. Other examples of amidine-containing compounds include methyl pyrimidine and 1,8-diamino octahydronaphthalene.

In another embodiment of a method of use, a method is provided for treating an animal, such as a mammal, for infection with, for example, a virus, a bacterium, or a parasite. The method comprises administering to the animal, e.g., the mammal, an amount of a diazeniumdiolate sufficient to treat the infection in the animal.

In yet another embodiment, a method for treating an animal, such as a mammal, for cancer is provided. The method comprises administering to the animal, e.g., the mammal, an amount of diazeniumdiolate sufficient to prevent the growth or metastasis of the cancer in the animal or to render it more susceptible to radiation or chemotherapy.

In another embodiment, a method is provided for treating an inanimate object for the presence of a potentially infectious virus, bacterium, or parasite. The method comprises contacting the inanimate object with an amount of a present inventive diazeniumdiolate sufficient to reduce the presence of the potentially infectious virus, bacterium or parasite. By "potentially infectious" is meant the capability of infecting an animal, such as a mammal.

It is contemplated that the diazeniumdiolates derived from enamines and amidines in accordance with the present invention can be used to coat prostheses, stents, and medical implants, such as breast implants, prior to surgical introduction into the body as a means of reducing the risk of solid state carcinogenesis associated therewith, or as a means of preventing adhesion of platelets to the implants. Additionally, the prostheses and implants can be manufactured using an enamine- or amidine-derived diazeniumdiolate as an integral component of the starting materials. Medical devices incorporating an enamine- or amidine-derived diazeniumdiolate provide an invaluable two-pronged approach to the treatment of many biological disorders, providing useful medical structures that also advantageously provide local release of NO.

The diazeniumdiolates derived from enamines and amidines also have utility in the in vitro study of NO biology.

EXAMPLES

The following examples further illustrate the present invention and, of course, should not be construed as in any way limiting its scope.

All melting points were determined on a hot stage and are uncorrected. The $^1H$ NMR spectra were determined at 200 MHz with a Varian XL-200 spectrometer and the $^{13}C$ NMR spectra were obtained at 50 MHz using the same instrument. The chemical shifts are expressed in δ values (ppm) relative to either tetramethylsilane or sodium 3-(trimethylsilyl) propionate-$d_4$ as internal standards. Elemental analyses were performed by Atlantic Microlabs, Inc. (Norcross, Ga.).

Except as noted here, all reagents and amines were obtained from Aldrich Chemical Company (Milwaukee, Wis.). Reaction solvents were Aldrich anhydrous grade but all others were reagent grade. Commercial grade nitric oxide was obtained from Matheson Gas Products and was used as received.

Reactions under pressure were conducted in standard glass hydrogenation bottles as previously described (Hrabie et al., *J. Org. Chem.* 58: 1472–1476 (1993)). The general directions are repeated here for completeness.

Given that stainless steel (SS) is required for prolonged exposure to NO gas and amines degrade most types of stoppers and gaskets, a specialized reactor modeled after the standard Parr 3911 hydrogenation apparatus (Parr Instrument Co., Moline, Ill.) was constructed. The reservoir was replaced by a type 304 SS gas sampling cylinder equipped with SS fittings (available from any "valve and fitting" plumbing supply company). The valves were diaphragm-seal packless type (Aldrich), and the pressure gauges were SS (Air Products). The usual Parr clamp and bottle system was employed but was connected to the gas reservoir via a Teflon tube and mounted to allow stirring with a magnetic stirrer.

All of the analytical data given were obtained using the products as isolated directly from the reaction mixtures.

Example 1

This example describes a generalized procedure for the preparation of NO- and/or $NO^-$-releasing compounds from amidines.

A solution of the appropriate amidine, which was obtained commercially (Aldrich) or synthesized in accordance with standard procedures, in the desired solvent was placed in a standard Parr hydrogenation bottle. Nitrogen was passed through the apparatus and bubbled through the solution for 5–10 min, the bottle was clamped, and NO gas was admitted to a pressure of 5 atm. The solution was stirred for the indicated time at room temperature with addition of NO as needed during the first 5–6 h to maintain the reservoir pressure. Excess NO was then vented and $N_2$ was bubbled through the resultant white slurry for 5 min. The product was isolated by filtration, washed with the reaction solvent, then washed with ether and dried in vacuo for several hours. All of the products were amorphous, voluminous white powders, which were air-stable but were stored in a refrigerator.

Example 2

This example describes the preparation of 2-methyl-2-imidazoline tetrakis(nitric oxide)adduct and its sodium salt.

A solution of 2-methyl-2-imidazoline (lysidine, 5.0 g, 59.4 mmol) in 150 ml acetonitrile was reacted with NO for 28 h as described above. Yield 3.59 g (49%); m.p. 102–103° C. dec.; $^1H$ NMR ($D_2O$) δ 1.92 (6H, s), 3.51 (8H, s), 3.67 (4H, s); $^{13}C$ NMR ($D_2O$) 24.8, 42.4, 42.5, 44.6, 51.3, 51.7, 163.5, 177.2; UV (0.01 N NaOH) $\lambda_{max}$ 260 nm, =13,600 $M^{-1}cm^{-1}$, 206 nm, ε=22,500. Anal. Calcd for $C_{12}H_{24}N_{10}O_4$: C, 38.71; H, 6.50; N, 37.61. Found: C, 38.92; H, 6.55; N, 37.62.

To prepare the disodium salt, 1.74 g of a 25% NaOMe in MeOH solution (Aldrich, 8.06 mmol) was diluted with 0.5 ml MeOH and to this was added 1.5 g of the above diimidazolinium salt (8.06 mmol). The solid slowly dissolved and then re-precipitated. The slurry was diluted with acetonitrile, filtered and the solid dried in vacuo to afford a white powder. Yield 0.92 g (92%). m.p. >180° C. (chars); $^1$H NMR (D$_2$O) δ 2.7–2.8 (2H, m), 3.3–3.4 (2H, m).

Example 3

This example describes the preparation of acetamidine tetrakis (nitric oxide) adduct.

A solution of acetamidine hydrochloride (7.0 g, 74.0 mmol) in 150 ml acetonitrile was treated with 16.93 ml of 25% NaOMe in MeOH (74.0 mmol) and the precipitated sodium chloride was removed by filtration. The resulting solution was treated with NO for 16 h to yield a tan powder. Yield 5.95 g (82%); m.p. >150° C. (chars); $^1$H NMR (D$_2$O) δ 2.21 (s); $^{13}$C NMR (D$_2$O) 20.8, 51.8, 57.7, 164.6.

Example 4

This example describes the preparation of 2-iminopiperidine bis(nitric oxide)adduct.

A solution of 2-iminopiperidine hydrochloride (5.0 g, 37.2 mmol) in 200 ml acetonitrile was treated with 8:5 ml of 25% NaOMe in MeOH (37.2 mmol) and 10 ml MeOH and the precipitated sodium chloride was removed by filtration. The resulting solution was treated with NO for 23 h to yield an off-white powder. Yield 4.5 g (95%); m.p. 110–112° C. (dec.); $^1$H NMR (D$_2$O) δ 1.8–1.9 (6H, m), 2.55–2.65 (2H, m), 2.85–2.95 (2H, m), 3.3–3.4 (2H, m), 3.5–3.6 (2H, m); $^{13}$C NMR (D$_2$O) 19.0, 20.3, 23.0, 28.3, 29.0, 43.7, 44.1, 90.6, 100.5, 162.6.

Example 5

This example describes the preparation of 2-cyclohexyl-2-imidazoline bis(nitric oxide)adduct.

The starting material for this preparation was produced by the method described by Neef et al. (J. Org. Chem. 46: 2824–2826 (1981)). A solution of 2-cyclohexyl-2-imidazoline (5.0 g, 32.8 mmol) in 300 ml acetonitrile was reacted with NO for 78 h. Yield 6.66 g (97%); m.p. 158–159° C. (dec.); $^1$H NMR (D$_2$O) δ 1.4–1.7 (6H, m), 1.9–2.1 (2H, m), 2.5–2.6 (2H, m), 4.0 (4H, s); $^{13}$C NMR (D$_2$O) 23.9 (2C), 26.6, 34.3 (2C), 47.3 (2C), 73.0, 173.4.

Example 6

This example describes the preparation of tetrahydrozoline bis(nitric oxide)adduct.

A solution of tetrahydrozoline hydrochloride (10.0 g, 42.25 mmol) in 9.66 ml of 25% NaOMe in MeOH (42.25 mmol NaOMe) was diluted with 200 ml acetonitrile and the precipitated sodium chloride was removed by filtration. The resulting solution was treated with NO for 24 h. Yield 9.0. g (82%); m.p. 168–169° C. (dec.); $^1$H NMR (D$_2$O) δ 1.8–1.9 (2H, m), 2.3–2.45 (1H, m), 2.9–3.0 (3H, m), 4.00 (4H, s), 7.15–7.47 (4H, m); $^{13}$C NMR (D$_2$O) 20.4, 30.6, 34.7, 47.7 (2C), 76.0, 129.7, 130.7, 131.8, 133.0, 133.1, 141.5, 173.7. Anal. Calcd. for C$_{13}$H$_{16}$N$_4$O$_2$: C, 59.99; H, 6.20; N, 21.52. Found: C, 60.05; H, 6.14; N, 21.48.

Example 7

This example describes the preparation of idazoxan-bis (nitric oxide) adduct available from Research Biochemicals, Inc. (Natick, Hi.).

A solution of idazoxan hydrochloride (1.00 g, 4.155 mmol) in a mixture of 0.95 ml 25% NaOMe in MeOH (4.155 mmol NaOMe) and 3 ml MeOH was diluted with 40 ml acetonitrile and the precipitated sodium chloride was removed by filtration. The resulting solution was treated with NO for 21 h. Yield 0.62 g (56%); m.p. 152–154° C. (dec.); $^1$H NMR (D$_2$O) δ 4.04 (4H, s), 4.64 (1H, d), 5.13 (1H, d), 7.02–7.22 (4H, m). Anal. Calcd. for C$_{13}$H$_{16}$N$_4$O$_2$: C, 49.81; H, 4.94; N, 21.12. Found: C, 50.22; H, 4.61; N, 20.98.

Example 8

This example describes a general procedure for preparation of diazeniumdiolate derivatives of enamines.

Enamines were prepared from an equimolar mixture of an aldehyde and ketone and a wide variety of secondary amines via dehydration. Such methods are described in Hicknott, Tetrahedron 38: 1975–2050, and 3363–3446 (1982); Cook, *Enamines: Synthesis, Structure and Reactions,* Marcel Dekker, New York (1988); and Szmuszkovicz, "Enamines", Chapter 4, *In advances in Org. Chem. Methods and Results,* Wiley Interscience, New York (1963). Preferred amines include dimethylamine, diethylamine, piperidine, pyrrolidine, morpholine and N-methyl-aniline.

These compounds were prepared according to the general procedure set forth in Example 1, except that the reactions were cooled when required and some gave crystalline products as indicated in the individual descriptions.

Example 9

This example describes the preparation of cyclohexanone morpholine enamine bis(nitric oxide) adduct.

A solution of the enamine derived from morpholine and cyclohexanone (15.0 g, 89.7 mmole) in 150 ml ethyl ether was cooled in dry ice without stirring and reacted with NO for 20 h as it warmed to room temperature. Workup as above produced large clear crystals of product. Yield 8.14 g (40%); m.p. 85–87° C.; $^1$H NMR (CD$_3$CN) δ 1.5–2.3 (6H, m), 2.44–2.55 (4H, m), 2.85–2.96 (4H, m), 5.13–5.18 (1H, m), 5.23–5.27 (1H, t), 11.6 (1H, br.s); $^{13}$C NMR (CD$_3$CN) 19.2, 24.7, 28.6, 50.6 (2C), 67.1, 67.5 (2C), 112.5, 141.3; exact mass calcd. for C$_{10}$H$_{17}$N$_3$O$_3$ (M$^+$) 227.1269, found 227.1254. Anal. Calcd. for C$_{10}$H$_{17}$N$_3$O$_3$: C, 52.85; H, 7.54; N, 18.49. Found: C, 53.32; H, 7.63; N, 18.76.

Example 10

This example describes the preparation of isobutyraldehyde morpholine enamine bis (nitric oxide) adduct.

A solution of the enamine derived from morpholine and isobutyraldehyde (7:0 g, 49.6 mmole) in 100 ml THF was reacted with NO for 22 h as described above. Yield 4.05 g (41%); m.p. 91–92° C.; $^1$H NMR (D$_2$O) δ 1.48 (6H, s), 3.25–3.31 (4H, m), 3.92–3.98 (4H, m) , 5.26 (1H, s); $^{13}$C NMR (D$_2$O) 23.2 (2C), 46.1 (2C), 66.6 (2C), 75.7, 95.2; exact mass calcd. for C$_8$H$_{16}$N$_3$O$_3$ (MH$^+$) 202.1192; found 202.1137. Anal. Calcd. for C$_8$H$_{15}$N$_3$O$_3$: C, 47.75; H. 7.51; N, 20.88. Found: C, 47.74; H, 7.70; N, 20.13.

Example 11

This example describes the preparation of cyclohexanecarboxaldehyde morpholine enamine bis (nitric oxide) adduct.

A solution of 4-(cyclohexylidenemethyl)morpholine (10.0 g, 55.2 mmol) in 200 mL of CH$_3$CN was cooled at 0° C. in an ice bath and reacted without tirring with NO as described above for 6 h and then warmed to room temperature. The product was isolated by filtration, washed with $CH_3CN$, then ether and dried in vacuo. Yield 7.13 g (54%); mp 115–117° C.; $^1H$ NMR δ 1.25–1.40 (2H, m), 1.48–1.70 (4H, m), 1.95–2.40 (4H, m), 3.20–3.26 (4H, m), 3.90–3.96 (4H, m), 5.05 (1H, s); $^{13}C$ NMR δ 24.1 (2C), 27.8, 31.3 (2C), 46.3 (2C), 67.1 (2C), 78.0, 95.7.

Anal. Calcd for $C_{11}H_{19}N_3O_2$: C, 54.76; H, 7.94; N, 17.41. Found: C, 54.93; H, 8.04; N, 17.60.

Example 12

This example describes the preparation of isobutyraldehyde piperidine enamine bis(nitric oxide) adduct (25).

A solution of the enamine derived from piperidine and isobutyraldehyde (5.0 g, 35.9 mmole). in 150 ml $CH_3CN$ was stirred at room temperature and reacted with NO for 23 h as described above. Yield 3.25 g (45%); m.p. 84–85° C.; $^1H$ NMR ($D_2O$) δ 1.48 (6H, s), 1.66–1.83 (6H, m), 3.13–3.18 (4H, m), 5.25 (1H, s). $^{13}C$ NMR ($D_2O$) 23.2 (2C), 24.3, 25.1 (2C), 47.4 (2C), 75.5, 95.2. Anal. Calcd. for $C_9H_{17}N_3O_2$: C, 54.25; H, 8.60; N, 21.09. Found: C, 52.69; H, 8.56; N, 21.28.

Example 13

This example describes the preparation of isobutyraldehyde pyrrolidine enamine bis (nitric oxide) adduct.

A solution of N-(2-methyl-1-propenyl)pyrrolidine (10.0 g, 79.9 mmol) in 200 mL of $CH_3CN$ was cooled to 0° C. in an ice bath and reacted without stirring with NO as described above for 6 h and then warmed to room temperature. The product was isolated by filtration, washed with $CH_3CN$, then ether and dried in vacuo. Yield 88.8 g (60%); mp 75–76° C.; $^1H$ NMR δ 1.48 (6H, s), 1.98–2.03 (4H, m), 3.23–3.32 (4H, m), 5.25 (1H, s); $^{13}C$ NMR δ 23.2 (2C), 26.5 (2C), 48.3 (2C), 75.6, 95.2.

Example 14

This example describes the preparation of isobutyraldehyde N-methylaniline enamine bis(nitric oxide) adduct.

A solution of the enamine derived from N-methylaniline and isobutyraldehyde (5.0 g, 31.0 mmole) in 150 ml $CH_3CN$ was stirred at room temperature and reacted with NO for 20 h. The resulting pale yellow solution was concentrated to dryness on a rotary evaporator and the residual solid was recrystallized from absolute ethanol to yield 2.26 g (33%) of product as pale, cream-colored needles. m.p. 83–84° C.; $^1H$ NMR ($CDCl_3$) δ 1.59 (3H, s), 1.63 (3H, s), 2.75. (3H, s), 6.00 (1H, s), 6.96–7.37 (5H, m); $^{13}C$ NMR ($CDCl_3$) 17.4, 26.8, 34.4, 75.6, 101.1, 118.9 (2C), 122.7, 129.4 (2C), 149.3. Anal. Calcd. for $C_{11}H_{15}N_3O_2$: C, 59.71; H, 6.83; N, 18.99. Found: C, 59.77; H, 6.84; N, 19.01.

Example 15

This example describes the preparation of isobutyraldehyde N-methyl-p-toluidine enamine bis(nitric oxide) adduct.

A solution of the enamine derived from N-methyl-p toluidine and isobutyraldehyde (5.0 g, 28.5 mmole) in 150 ml $CH_3CN$ was stirred at room temperature and reacted with NO for 20 h. The resulting pale yellow-orange solution was concentrated to dryness on a rotary evaporator and the residual off-white solid was recrystallized from absolute ethanol to yield 2.21 g (33%) of product as white cotton-like needles. m.p. 127–128° C.; $^1H$ NMR ($CDCl_3$) δ 1.58 (3H, s), 1.61 (3H, s) , 2.31 (3H, s), 2.71 (3H, s), 5.92 (1H, s), 6.90–7.15 (4H, m); $^{13}C$ NMR ($CDCl_3$) 17.3, 20.5, 26.8, 34.9, 75.4, 101.9, 119.7 (2C), 129.9 (2C), 132.7, 147.2. Anal. Calcd. for $C_{12}H_{17}N_3O_2$: C, 61.26; H, 7.28; N, 17.86. Found: C, 61.32; H, 7.35; N, 17.88.

Example 16

This example describes the preparation of isobutyraldehyde N-methyl-p-anisidine enamine bis (nitric oxide) adduct.

A solution of the enamine derived from N-methyl-p-anisidine and isobutyraldehyde (5.0 g, 26.1 mmole) in 150 ml $CH_3CN$ was stirred at room temperature and reacted with NO for 23 h. The resulting pale brown solution was concentrated to dryness on a rotary evaporator and the residual oil was crystallized from absolute ethanol to yield 4.89 g (75%) of product as colorless chunky crystals. m.p. 97–98° C.; $^1H$ NMR ($CDCl_3$) δ 1.58 (3H, s), 1.60 (3H, s), 2.67 (3H, s); 3.79 (3H, s), 5.80 (1H, s), 6.84–7.06 (4H, m); $^{13}C$ NMR ($CDCl_3$) 17.2, 26.8, 36.1, 55.5, 75.2, 103.0, 114.6 (2C), 122.8 (2C), 143.4, 156.3. Anal. Calcd. for $C_{12}H_{17}N_3O_3$: C, 57.35; H, 6.82; N, 16.72. Found: C, 57.36; H, 6.87; N, 16.75.

Example 17

This example describes the measurement of the production of NO and $N_2O$ by amidine/nitric oxide adducts.

As a demonstration of the efficacy of the amidine/nitric oxide adducts described herein as nitric oxide and nitroxyl releasing agents, selected compounds were dissolved in either 0.1 N HCl or pH 7.4 buffer and the headspace was monitored by chemiluminescence (to detect NO) and gas chromatography (to detect $N_2O$, the dehydrated dimer of HNO). The results are shown in Table I.

TABLE I

| Cmpd of Ex. No. | Solution | Ratio $N_2O$:NO | Yield (in moles per mole cmpd) | |
|---|---|---|---|---|
| | | | $N_2O$ | NO |
| 2 | 0.1 N HCl | 2:1 | 0.9 | 0.45 |
| 3 | pH 7.4 | 13:1 | 0.64 | 0.05 |
| 4 | pH 7.4 | 6:1 | 0.45 | −0.08 |
| 5 | 0.1 N HCl | — | 0.2 | N.D.* |
| 6 | pH 7.4 | — | 0.4 | N.D.* |

*The compounds of Examples 5 and 6 released NO too slowly for practical measurement by headspace analysis.

Example 18

This example describes the measurement of the time course of NO production by amidine and enamine nitric oxide adducts.

To demonstrate the utility of these compounds as long-term nitric oxide releasing agents, selected compounds were dissolved in phosphate buffer at pH 7.4 and incubated in a 37° C. thermostated water bath. The NO release rate was measured periodically by flushing the solution with inert $N_2$ gas and then sweeping newly generated NO into a chemiluminescence detector and integrating the signal produced over the next 4–7 mins. NO release was measured over a period of two weeks.

None of these compounds released nitric oxide via a single pathway which produced a release profile consistent with first order kinetics. Accordingly, the results of each test are summarized here by giving the initial NO release rate, the rate at one intermediate timepoint and the total time of observed NO release for representative examples.

Thus, the compound of Example V (tetrahydrozoline diazeniumdiolate) showed an initial NO release rate of 3.64×10⁻¹¹ moles NO per minute per milligram of dissolved sample which decreased to 2.06×10⁻¹¹ moles NO per min. per mg. after 7 days and continued for several weeks although the last quantitative measurement showed an NO release rate of 9.00×10⁻¹² moles NO per min. per mg. 15 days after the beginning of the experiment.

Likewise, the compound of Example VI (idazoxan diazeniumdiolate) showed an initial NO release rate of 5.25×10⁻¹¹ moles NO/min./mg. which gradually increased to 1.41×10⁻¹⁰ moles NO/min./mg. after 4 days and then gradually decreased, reaching zero (i.e., no more NO was being given off) by day 16.

Among the enamine-derived compounds, the compound of Example VII (the diazeniumdiolate of the morpholine enamine of cyclohexanone) showed an initial NO release rate of 4.2×10⁻¹¹ mole NO/min./mg. which decreased with nearly first order kinetics to 1.8×10⁻¹¹ mole NO/min./mg. after 3 days and reached zero by day 7.

The enamine-derived diazeniumdiolate of Example VIII (from the morpholine enamine of isobutyraldehyde) showed an initial NO release rate of 3.7×10⁻¹¹ mole NO/min./mg. which rapidly decreased to a rate of 7.0×10⁻¹² mole NO/min./mg. and then remained at about this level for 4 days before slowly declining, reaching zero after 7 days.

All publications cited herein are hereby incorporated by reference to the same extent as if each publication were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A compound having the chemical structural linkage as follows:

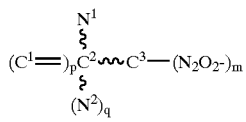

wherein
$C^2$~$C^3$ means either $C^2$—$C^3$ or $C^2$=$C^3$
m is 1 or 2
q is 0 or 1
p is 0 or 1
provided that
(1) $C^2$ is tetravalent, and bound to two or more of $C^1$, $C^3$, $N^1$ and $N^2$;
(2) when p=1, then q=0 and $C^2$~$C^3$ means $C^2$—$C^3$; or
(3) when p=0, and q=1, then $C^2$~$C^3$ means either (i) $C^2$=$C^3$ or (ii) $C^2$—$C^3$ where $C^2$~$N^1$ means $C^2$=$N^1$;
(4) when $C^2$~$C^3$ means $C^2$—$C^3$ and q=1 and p=0;
wherein $C^2$~$N^1$ and $C^2$~$N^2$ means

2. A compound selected from the group consisting of:

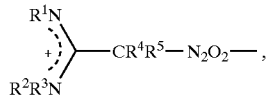
FORMULA I

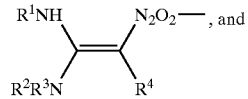
FORMULA II

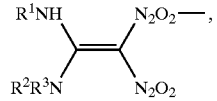
FORMULA III wherein
$R^1$—$R^3$ are independently hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted $C_{3-8}$ cycloalkyl, a $C_{3-8}$ heterocyclic ring bound through a carbon atom and in which the heteroatom is oxygen or nitrogen, a substituted or unsubstituted naphthyl, a substituted or unsubstituted tetrahydronaphthyl, a substituted or unsubstituted octahydronaphthyl, benzyl or substituted benzyl, substituted with up to three substituents, or phenyl or substituted phenyl, substituted with up to three substituents;
$R^4$ and $R^5$ are independently chosen from hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted benzyl, an unsubstituted or substituted phenyl, a substituted or unsubstituted piperazino, a substituted or unsubstituted morpholino, amino, an unsubstituted or substituted alkylamino, an unsubstituted or substituted arylamino, an unsubstituted or substituted dialkylamino, an unsubstituted or substituted diarylamino, carboxyalkylamino, carboxydialkylamino, unsubstituted or substituted tolyl, xylyl, anisyl, mesityl, an unsubstituted or substituted acetyl, an unsubstituted or substituted acetoxy, carboxy, an unsubstituted or substituted carboxymethyl, an unsubstituted or substituted carboxyethyl, an unsubstituted or substituted alkylcarbonyl, thiol, an unsubstituted or substituted alkylthio, an unsubstituted or substituted alkoxy, carboxamido, an unsubstituted or substituted alkylcarboxamido, or an unsubstituted or substituted dialkylcarboxamido, an unsubstituted or substituted phenoxy, an unsubstituted or substituted benzyloxy, phenylcarbonyl, benzylcarbonyl, an unsubstituted or substituted nitrophenyl, trialkylsilyl or nitro; and
$R^1$ and $R^2$ together with the nitrogen atoms to which they are bonded form a substituted or unsubstituted $C_{2-8}$ heterocyclic ring, or
$R^2$ and $R^3$ together with the nitrogen atom to which they are bonded form a substituted or unsubstituted $C_{3-8}$ heterocyclic ring, or
$R^1$ and $R^4$ together with the nitrogen atom to which $R^1$ is bonded and with the carbon atom to which $R^4$ is bonded and with the intervening carbon atom form a substituted or unsubstituted $C_{2-6}$ heterocyclic ring, or $R^4$ and $R^5$ together with the carbon atom to which they are bonded form an unsubstituted or substituted $C_{3-8}$ cycloalkyl, or a $C_{4-8}$ heterocyclic ring in which the heteroatom is selected from the group consisting of oxygen, nitrogen, and sulfur, or $R^4$ and $R^5$ together with the carbon atom to which they are bonded form an unsubstituted or substituted 1,4-benzodioxane, 1,3-benzodioxole, tetrahydronaphthlene, octahydronaphthalene, piperazine, morpholine, tetrahydroquinoline, tetrahydroquinoxaline, tetrahydroisoquinoline;

with the proviso that the heterocyclic ring formed by $R^1$ and $R^2$, $R^2$ and $R^3$, $R^1$ and $R^4$, or $R^4$ and $R^5$ is not a five-membered heterocyclic ring in which the heteroatom is oxygen, nitrogen, or sulfur, or six-membered heterocyclic ring in which the heteroatom is nitrogen.

3. The compound of claim 2 of

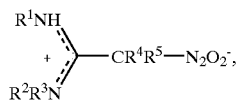

FORMULA I wherein $R^1$—$R^3$ are independently hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted $C_{3-8}$ cycloalkyl, a $C_{3-8}$ heterocyclic ring bound through a carbon atom and in which the heteroatom is oxygen or nitrogen, a substituted or unsubstituted naphthyl, a substituted or unsubstituted tetrahydronaphthyl, a substituted or unsubstituted octahydronaphthyl, benzyl or substituted benzyl, substituted with up to three substituents, or phenyl or substituted phenyl, substituted with up to three substituents;

$R^4$ and $R^5$ are independently chosen from hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted benzyl, an unsubstituted or substituted phenyl, a substituted or unsubstituted piperazino, a substituted or unsubstituted morpholino, amino, an unsubstituted or substituted alkylamino, an unsubstituted or substituted arylamino, an unsubstituted or substituted dialkylamino, an unsubstituted or substituted diarylamino, carboxyalkylamino, carboxydialkylamino, unsubstituted or substituted tolyl, xylyl, anisyl, mesityl, an unsubstituted or substituted acetyl, an unsubstituted or substituted acetoxy, carboxy, an unsubstituted or substituted carboxymethyl, an unsubstituted or substituted carboxyethyl, an unsubstituted or substituted alkylcarbonyl, thiol, an unsubstituted or substituted alkylthio, an unsubstituted or substituted alkoxy, carboxamido, an unsubstituted or substituted alkylcarboxamido, or an unsubstituted or substituted dialkylcarboxamido, an unsubstituted or substituted phenoxy, an unsubstituted or substituted benzyloxy, phenylcarbonyl, benzylcarbonyl, an unsubstituted or substituted nitrophenyl, trialkylsilyl or nitro; and $R^1$ and $R^2$ together with the nitrogen atoms to which they are bonded form a substituted or unsubstituted $C_{2-8}$ heterocyclic ring, or $R^2$ and $R^3$ together with the nitrogen atom to which they are bonded form a substituted or unsubstituted $C_{3-8}$ heterocyclic ring, a substituted or unsubstituted $C_{3-8}$ heterocyclic ring, or $R^1$ and $R^4$ together with the nitrogen atom to which $R^1$ is bonded and with the carbon atom to which $R^4$ is bonded and with the intervening carbon atom form a substituted or unsubstituted $C_{2-6}$ heterocyclic ring, or $R^4$ and $R^5$ together with the carbon atom to which they are bonded form an unsubstituted or substituted $C_{3-8}$ cycloalkyl, or a $C_{4-8}$ heterocyclic ring in which the heteroatom is selected from the group consisting of oxygen, nitrogen, and sulfur, or $R^4$ and $R^5$ together with the carbon atom to which they are bonded form an unsubstituted or substituted 1,4-benzodioxane, 1,3-benzodioxole, tetrahydronaphthlene, octahydronaphthalene, piperazine, morpholine, tetrahydroquinoline, tetrahydroquinoxaline, tetrahydroisoquinoline;

with the proviso that the heterocyclic ring formed by $R^1$ and $R^2$, $R^2$ and $R^3$, $R^1$ and $R^4$, or $R^4$ and $R^5$ is not a five-membered heterocyclic ring in which the heteroatom is oxygen, nitrogen, or sulfur, or six-membered heterocyclic ring in which the heteroatom is nitrogen.

4. The compound of claim 2 of

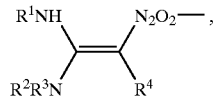

FORMULA II wherein $R^1$—$R^3$ are independently hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted $C_{3-8}$ cycloalkyl, a substituted or unsubstituted $C_{3-8}$ heterocyclic ring bound through a carbon atom and in which the heteroatom is oxygen or nitrogen, a substituted or unsubstituted naphthyl, a substituted or unsubstituted tetrahydronaphthyl, a substituted or unsubstituted octahydronaphthyl, benzyl or substituted benzyl, substituted with up to three substituents, or phenyl or substituted phenyl, substituted with up to three substituents;

$R^4$ is hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted benzyl, an unsubstituted or substituted phenyl, a substituted or unsubstituted piperazino, a substituted or unsubstituted morpholino, amino, an unsubstituted or substituted alkylamino, an unsubstituted or substituted arylamino, an unsubstituted or substituted dialkylamino, an unsubstituted or substituted diarylamino, carboxyalkylamino, carboxydialkylamino, unsubstituted or substituted tolyl, xylyl, anisyl, mesityl, an unsubstituted or substituted acetyl, an unsubstituted or substituted acetoxy, carboxy, an unsubstituted or substituted carboxymethyl, an unsubstituted or substituted carboxyethyl, an unsubstituted or substituted alkylcarbonyl, thiol, an unsubstituted or substituted alkylthio, an unsubstituted or substituted alkoxy, carboxamido, an unsubstituted or substituted alkylcarboxamido, or an unsubstituted or substituted dialkylcarboxamido, an unsubstituted or substituted phenoxy, an unsubstituted or substituted benzyloxy, phenylcarbonyl, benzylcarbonyl, an unsubstituted or substituted nitrophenyl, trialkylsilyl or nitro; and $R^1$ and $R^2$ together with the nitrogen atoms to which they are bonded form a substituted or unsubstituted $C_{3-8}$ heterocyclic ring, or $R^2$ and $R^3$ together with the nitrogen atom to which they are bonded form a substituted or unsubstituted $C_{3-8}$ heterocyclic ring, or $R^1$ and $R^4$ together with the nitrogen atom to which $R^1$ is bonded and with the carbon atom to which $R^4$ is bonded and with the intervening carbon atom form a substituted or unsubstituted $C_{2-6}$ heterocyclic ring;

with the proviso that the heterocyclic ring formed by $R^1$ and $R^2$, $R^2$ and $R^3$, or $R^1$ and $R^4$ is not a five-membered heterocyclic ring in which the heteroatom is oxygen, nitrogen, or sulfur, or six-membered heterocyclic ring in which the heteroatom is nitrogen.

5. The compound of claim 2 of

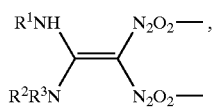

FORMULA III wherein $R^1$—$R^3$ are independently hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted $C_{3-8}$ cycloalkyl, a $C_{3-8}$ heterocyclic ring bound through a carbon atom and in which the heteroatom is oxygen or nitrogen, a substituted or unsubstituted naphthyl, a substituted or unsubstituted tetrahydronaphthyl, a substituted or unsubstituted octahydronaphthyl, benzyl or substituted benzyl, substituted with up to three substituents, or phenyl or substituted phenyl, substituted with up to three substituents; and $R^1$ and $R^2$ together with the nitrogen atoms to which they are bonded form a substituted or unsubstituted $C_{2-8}$ heterocyclic ring, or $R^2$ and $R^3$ together with the nitrogen atom to which they are bonded form a substituted or unsubstituted $C_{3-8}$ heterocyclic ring;

with the proviso that the heterocyclic ring formed by $R^1$ and $R^2$, or $R^2$ and $R^3$ is not a five-membered heterocyclic ring in which the heteroatom is oxygen, nitrogen, or sulfur, or six-membered heterocyclic ring in which the heteroatom is nitrogen.

6. The compound of Formulae I, II or III of claim 2 wherein the substituents on the substituted groups are selected from the group consisting of alkoxy, acyloxy, hydroxy, halo, benzyl, acetyl, carboxyl, carboxyalkyl, carboxyalkylamido, carboxydialkylamido, alkylcarbonyl, arylamino, diarylamino, cyano, tolyl, xylyl, mesityl, anisyl, carboxamido, amino, alkylamino, dialkylamino, formyl, dioxane, thiol, alkylthiol, aryl, heteroaryl, or phenoxy, benzyloxy, phenylcarbonyl, benzylcarbonyl, nitrophenyl, trialkylsilyl, nitro, sulfonyl, nitrobenzyl, trialkylammonium, alkyl, cycloalkyl, tetrahydrofuranyl, tetrahydropyranyl, piperidine and morpholine.

7. The compound of claim 3, wherein the substituents on the substituted groups are selected from the group consisting of alkoxy, acyloxy, hydroxy, halo, benzyl, acetyl, carboxyl, carboxyalkyl, carboxyalkylamido, carboxydialkylamido, alkylcarbonyl, arylamino, diarylamino, cyano, tolyl, xylyl, mesityl, anisyl, carboxamido, amino, alkylamino, dialkylamino, formyl, dioxane, thiol, alkylthiol, aryl, heteroaryl, or phenoxy, benzyloxy, phenylcarbonyl, benzylcarbonyl, nitrophenyl, trialkylsilyl, nitro, sulfonyl, nitrobenzyl, trialkylammonium, alkyl, cycloalkyl, tetrahydrofuranyl, tetrahydropyranyl, piperidine and morpholine.

8. The compound of claim 4, wherein the substituents on the substituted groups are selected from the group consisting of alkoxy, acyloxy, hydroxy, halo, benzyl, acetyl, carboxyl, carboxyalkyl, carboxyalkylamido, carboxydialkylamido, alkylcarbonyl, arylamino, diarylamino, cyano, tolyl, xylyl, mesityl, anisyl, carboxamido, amino, alkylamino, dialkylamino, formyl, dioxane, thiol, alkylthiol, aryl, heteroaryl, or phenoxy, benzyloxy, phenylcarbonyl, benzylcarbonyl, nitrophenyl, trialkylsilyl, nitro, sulfonyl, nitrobenzyl, trialkylammonium, alkyl, cycloalkyl, tetrahydrofuranyl, tetrahydropyranyl, piperidine and morpholine.

9. The compound of claim 5, wherein the substituents on the substituted groups are selected from the group consisting of alkoxy, acyloxy, hydroxy, halo, benzyl, acetyl, carboxyl, carboxyalkyl, carboxyalkylamido, carboxydialkylamido, alkylcarbonyl, arylamino, diarylamino, cyano, tolyl, xylyl, mesityl, anisyl, carboxamido, amino, alkylamino, dialkylamino, formyl, dioxane, thiol, alkylthiol, aryl, heteroaryl, or phenoxy, benzyloxy, phenylcarbonyl, benzylcarbonyl, nitrophenyl, trialkylsilyl, nitro, sulfonyl, nitrobenzyl, trialkylammonium, alkyl, cycloalkyl, tetrahydrofuranyl, tetrahydropyranyl, piperidine and morpholine.

10. The compound of claim 2 of Formulae I, II or III, wherein the substituent on the substituted groups is a heteroaryl selected from the group consisting of pyrrole, furan, thiophene, thiazole, pyrazole, pyran, pyridine, and pyrimidine.

11. The compound of claim 7, wherein the substituent on the substituted groups is a heteroaryl selected from the group consisting of pyrrole, furan, thiophene, thiazole, pyrazole, pyran, pyridine, and pyrimidine.

12. The compound of claim 8, wherein the substituent on the substituted groups is a heteroaryl selected from the group consisting of pyrrole, furan, thiophene, thiazole, pyrazole, pyran, pyridine, and pyrimidine.

13. The compound of claim 9, wherein the substituent on the substituted groups is a heteroaryl selected from the group consisting of pyrrole, furan, thiophene, thiazole, pyrazole, pyran, pyridine, and pyrimidine.

14. The compound of claim 2 of Formulae I, II or III, wherein the substituents on the substituted groups are selected from the group consisting of benzyl, tolyl, carboxyl, carboxyalkyl, dialkylamino, arylamino, and diarylamino.

15. The compound of claim 3, wherein the substituents on the substituted groups are selected from the group consisting of benzyl, tolyl, carboxyl, carboxyalkyl, dialkylamino, arylamino, and diarylamino.

16. The compound of claim 4, wherein the substituents on the substituted groups are selected from the group consisting of benzyl, tolyl, carboxyl, carboxyalkyl, dialkylamino, arylamino, and diarylamino.

17. The compound of claim 5, wherein the substituents on the substituted groups are selected from the group consisting of benzyl, tolyl, carboxyl, carboxyalkyl, dialkylamino, arylamino, and diarylamino.

18. The compound of claim 5, wherein $R^1$ and $R^2$ are hydrogen and $R^3$ is the entire substituent attached to an amine of a compound selected from the group consisting of an amino acid, tryptamine, serotonin, histamine, valcyclovir, adenosine, thyroxine, guanine, guanosine, ubenimex, glucosamine, mannosamine, mycosamine, sphingosine, thienamycin, penicillamine and rimantadine.

19. The compound of claim 18, wherein the amino acid is selected from the group consisting of lysine, tryptophan and hydroxy-tryptophan.

20. A compound selected from the group consisting of

FORMULA IV

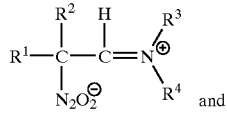

and

FORMULA V

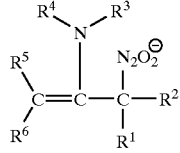

wherein $R^1$, $R^2$, $R^5$ and $R^6$ are independently hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted benzyl, a substituted or unsubstituted phenyl, a substituted or unsubstituted piperazino, a substituted or unsubstituted morpholino, amino, an unsubstituted or substituted alkylamino, an unsubstituted or substituted arylamino, an unsubstituted or substituted dialkylamino, an unsubstituted or substituted diarylamino, carboxyalkylamino, carboxydialkylamino, cyano, a substituted or unsubstituted tolyl, xylyl, anisyl, mesityl, an unsubstituted or substituted acetyl, an unsubstituted or substituted acetoxy, carboxy, an unsubstituted or substituted carboxymethyl, an unsubstituted or substituted carboxyethyl, an unsubstituted or substituted alkylcarbonyl, thiol, an unsubstituted or substituted alkylthio, an unsubstituted or substituted alkoxy, carboxamido, an unsubstituted or substituted alkylcarboxamido, or an unsubstituted or substituted dialkylcarboxamido, a substituted or unsubstituted phenoxy, a substituted or unsubstituted benzyloxy, phenylcarbonyl, benzylcarbonyl, a substituted or unsubstituted nitrophenyl, trialkylsilyl or nitro, $R^1$ and $R^2$ together with the carbon to which they are bonded can form a substituted or unsubstituted $C^4$–$C^8$ cycloalkyl, $R^2$ and $R^3$ together with the nitrogen atom to which they are bonded form a substituted or unsubstituted $C_{3-8}$ cycloalkyl, $R^3$ and $R^4$ are an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted $C_{3-8}$ cycloalkyl, a substituted or unsubstituted $C_{3-8}$ heterocyclic ring bound through a carbon atom and in which the heteroatom is oxygen or nitrogen, a substituted or unsubstituted naphthyl, a substituted or unsubstituted tetrahydronaphthyl, a substituted or unsubstituted octahydronaphthyl, benzyl or substituted benzyl, substituted with up to three substituents, or phenyl or substituted phenyl, substituted with up to three substituents, or $R^3$ and $R^4$ together with the nitrogen atom to which they are bonded can form a $C_{3-8}$ heterocyclic ring or a $C_{3-8}$ substituted heterocyclic ring or a $C_{3-8}$ unsubstituted or substituted heterocyclic ring containing up to two additional heteroatoms selected from the group O, S, N, or $R^1$ and $R^6$ together with the C=C—C through which they are bonded form an unsubstituted or substituted cycloalkyl, or $R^5$ and $R^6$ together with the carbon to which they are bonded can form a substituted or unsubstituted $C_{4-8}$ cycloalkyl.

21. A compound of

FORMULA IV

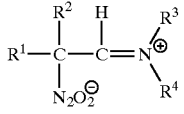

wherein $R^1$ and $R^2$ are independently hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted benzyl, a substituted or unsubstituted phenyl, a substituted or unsubstituted piperazino, a substituted or unsubstituted morpholino, amino, an unsubstituted or substituted alkylamino, an unsubstituted or substituted arylamino, an unsubstituted or substituted dialkylamino, an unsubstituted or substituted diarylamino, carboxyalkylamino, carboxydialkylamino, cyano, a substituted or unsubstituted tolyl, xylyl, anisyl, mesityl, an unsubstituted or substituted acetyl, an unsubstituted or substituted acetoxy, carboxy, an unsubstituted or substituted carboxymethyl, an unsubstituted or substituted carboxyethyl, an unsubstituted or substituted alkylcarbonyl, thiol, an unsubstituted or substituted alkylthio, an unsubstituted or substituted alkoxy, carboxamido, an unsubstituted or substituted alkylcarboxamido, or an unsubstituted or substituted dialkylcarboxamido, a substituted or unsubstituted phenoxy, a substituted or unsubstituted benzyloxy, phenylcarbonyl, benzylcarbonyl, a substituted or unsubstituted nitrophenyl, trialkylsilyl or nitro, $R^3$ and $R^4$ are an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted $C_{3-8}$ cycloalkyl, a substituted or unsubstituted $C_{3-8}$ heterocyclic ring bound through a carbon atom and in which the heteroatom is oxygen or nitrogen, a substituted or unsubstituted naphthyl, a substituted or unsubstituted tetrahydronaphthyl, a substituted or unsubstituted octahydronaphthyl, benzyl or substituted benzyl, substituted with up to three substituents, or phenyl or substituted phenyl, substituted with up to three substituents.

22. A compound of

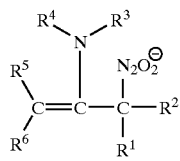

FORMULA V wherein $R^5$ and $R^6$ are independently hydrogen, an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted benzyl, a substituted or unsubstituted phenyl, a substituted or unsubstituted piperazino, a substituted or unsubstituted morpholino, amino, an unsubstituted or substituted alkylamino, an unsubstituted or substituted arylamino, an unsubstituted or substituted dialkylamino, an unsubstituted or substituted diarylamino, carboxyalkylamino, carboxydialkylamino, cyano, a substituted or unsubstituted tolyl, xylyl, anisyl, mesityl, an unsubstituted or substituted acetyl, an unsubstituted or substituted acetoxy, carboxy, an unsubstituted or substituted carboxymethyl, an unsubstituted or substituted carboxyethyl, an unsubstituted or substituted alkylcarbonyl, thiol, an unsubstituted or substituted alkylthio, an unsubstituted or substituted alkoxy, carboxamido, an unsubstituted or substituted alkylcarboxamido, or an unsubstituted or substituted dialkylcarboxamido, a substituted or unsubstituted phenoxy, a substituted or unsubstituted benzyloxy, phenylcarbonyl, benzylcarbonyl, a substituted or unsubstituted nitrophenyl, trialkylsilyl or nitro, $R^3$ and $R^4$ are an unsubstituted or substituted $C_{1-12}$ straight chain alkyl, an unsubstituted or substituted $C_{3-12}$ branched chain alkyl, an unsubstituted or substituted $C_{3-12}$ straight chain olefinic, an unsubstituted or substituted $C_{3-12}$ branched chain olefinic, a substituted or unsubstituted $C_{3-8}$ cycloalkyl, a substituted or unsubstituted $C_{3-8}$ heterocyclic ring bound through a carbon atom and in which the heteroatom is oxygen or nitrogen, a substituted or unsubstituted naphthyl, a substituted or unsubstituted tetrahydronaphthyl, a substituted or unsubstituted octahydronaphthyl, benzyl or substituted benzyl, substituted with up to three substituents, or phenyl or substituted phenyl, substituted with up to three substituents.

23. The compound of claim 22, wherein $R^2$ and $R^3$, together with the carbon and nitrogen atom to which they are bonded, form a $C_{3-8}$ cycloalkyl.

24. The compound of claim 23, wherein the $C_{3-8}$ cycloalkyl is substituted with a heteroatom.

25. The compound of claim 22, wherein $R^5$ and $R^6$, together with the C=C—C through which they are bonded, form a $C_{3-12}$ alicyclic hydrocarbon.

26. The compound of claim 21, wherein $R^3$ and $R^4$, together with the nitrogen to which they are bonded, form a $C_{3-8}$ cycloalkyl.

27. The compound of claim 26, wherein the $C_{3-8}$ cycloalkyl is further substituted with an unsubstituted or substituted heteroatom or an aromatic ring, optionally substituted with a $C_{1-6}$ alkyl or a $C_{1-6}$ alkoxy, and $R^1$ and $R^2$ optionally together form a $C_{3-8}$ cycloalkyl.

28. A method of treating an animal having a biological disorder treatable with nitric oxide, which method comprises administering to the animal a compound of claim 1 in an amount sufficient to treat the biological disorder in the animal.

29. The method of claim 28, wherein the biological disorder is restenosis.

* * * * *